United States Patent
Blackwell

(10) Patent No.: US 10,299,518 B2
(45) Date of Patent: May 28, 2019

(54) DRAIN SUPPORT APRON

(71) Applicant: Lea M. Blackwell, Fort Myers, FL (US)

(72) Inventor: Lea M. Blackwell, Fort Myers, FL (US)

(*) Notice: Subject to any disclaimer, the term of this patent is extended or adjusted under 35 U.S.C. 154(b) by 0 days.

(21) Appl. No.: 15/798,497

(22) Filed: Oct. 31, 2017

(65) Prior Publication Data
US 2018/0360133 A1    Dec. 20, 2018

Related U.S. Application Data

(63) Continuation-in-part of application No. 15/627,770, filed on Jun. 20, 2017.

(51) Int. Cl.
| | | |
|---|---|---|
| *A41C 3/00* | (2006.01) |
| *A61M 1/00* | (2006.01) |
| *A61M 27/00* | (2006.01) |
| *A41D 13/12* | (2006.01) |

(52) U.S. Cl.
CPC ......... *A41C 3/0064* (2013.01); *A61M 1/0003* (2013.01); *A61M 27/00* (2013.01); *A41C 3/0035* (2013.01); *A41D 13/1245* (2013.01); *A61M 2205/075* (2013.01); *A61M 2209/088* (2013.01)

(58) Field of Classification Search
CPC .. A61F 5/449; A61F 5/44; A61F 2013/15073; A61F 5/05825; A61F 5/02; A61M 1/0009; A41D 13/1245
USPC .... 2/314, 312, 311, 315–319, 333, 48, 49.2, 2/50, 51; 604/174, 179, 356, 357, 345; 224/191, 223, 660, 904
See application file for complete search history.

(56) References Cited

U.S. PATENT DOCUMENTS

| | | | | |
|---|---|---|---|---|
| 4,369,526 A * | 1/1983 | Clutts | ............... | A41D 13/0012 2/102 |
| 4,819,846 A * | 4/1989 | Hannemann | ............... | A45F 5/00 2/312 |
| 5,800,245 A * | 9/1998 | Barbe-Vicuna | ...... | A41C 3/0064 2/267 |
| 5,970,526 A * | 10/1999 | Weathers | ................ | A41F 9/002 2/311 |
| 6,032,289 A * | 3/2000 | Villapiano | ......... | A41D 13/1245 2/102 |
| 6,168,578 B1 * | 1/2001 | Diamond | ................ | A61M 1/28 2/312 |
| 6,390,885 B1 * | 5/2002 | Brooks | ................ | A41C 3/0064 450/1 |
| 6,682,507 B2 * | 1/2004 | Irish | ..................... | A61M 1/285 604/179 |
| 7,219,373 B2 * | 5/2007 | McNamara | ........ | A41D 13/0012 2/247 |
| 8,316,469 B2 * | 11/2012 | Miller | ..................... | A41D 1/08 2/227 |
| 8,790,154 B2 * | 7/2014 | Blackwell | ........... | A41C 3/0064 450/58 |
| 9,277,773 B2 * | 3/2016 | Blackwell | ........... | A41C 3/0064 |
| 9,578,902 B2 * | 2/2017 | Blackwell | ........... | A41C 3/0064 |
| 9,854,851 B2 * | 1/2018 | Blackwell | ........... | A41C 3/0064 |

(Continued)

*Primary Examiner* — Gloria M Hale
(74) *Attorney, Agent, or Firm* — Edward M. Livingston, Esq.; Bryan L. Loeffler, Esq.; Livingston Loeffler, P.A.

(57) ABSTRACT

A drain support apron (1) having a main panel (2) with a plurality of pockets (9) located thereon that provide storage for one or more drain bulbs (10). The drain apron is preferably worn around a patient's midsection.

1 Claim, 4 Drawing Sheets

(56) References Cited

U.S. PATENT DOCUMENTS

| | | | |
|---|---|---|---|
| 2003/0131398 A1* | 7/2003 | Haines | A45F 5/02 |
| | | | 2/312 |
| 2003/0182715 A1* | 10/2003 | Wallace | A41F 9/025 |
| | | | 2/338 |
| 2003/0191433 A1* | 10/2003 | Prentiss | A61M 1/06 |
| | | | 604/74 |
| 2012/0110714 A1* | 5/2012 | Pokorny | A41D 13/04 |
| | | | 2/48 |
| 2012/0159684 A1* | 6/2012 | Jiang | B82Y 10/00 |
| | | | 2/69 |
| 2012/0159694 A1* | 6/2012 | Ploughman | A41F 9/002 |
| | | | 2/321 |
| 2013/0171911 A1* | 7/2013 | Swendseid | A41C 3/0028 |
| | | | 450/85 |
| 2014/0302748 A1* | 10/2014 | Blackwell | A41C 3/0064 |
| | | | 450/58 |

* cited by examiner

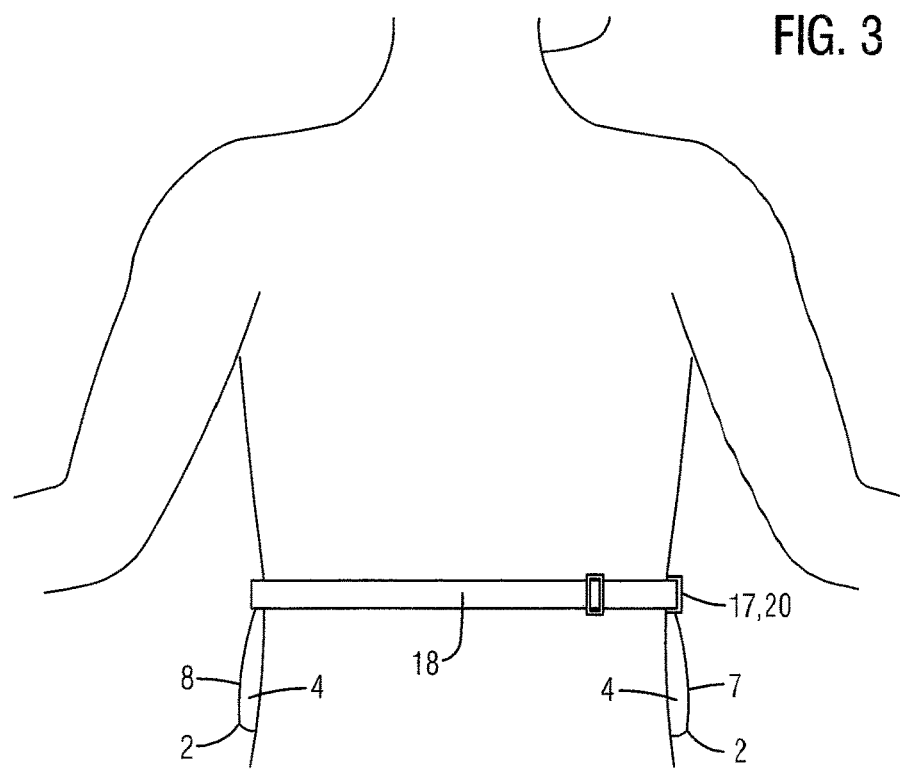
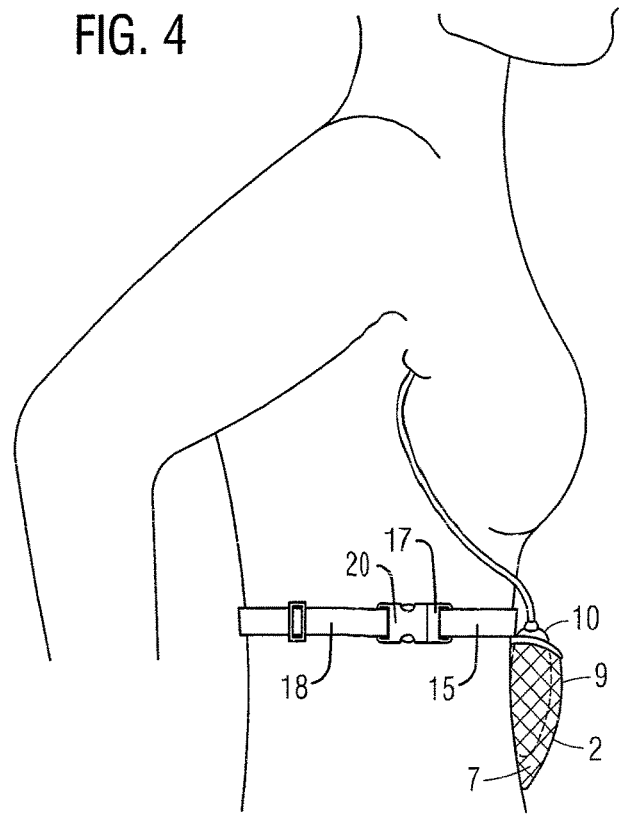

DRAIN SUPPORT APRON

CROSS-REFERENCE TO RELATED APPLICATIONS

This application is a continuation in part of application Ser. No. 15/627,770 filed on Jun. 20, 2017, which is currently pending and is a continuation of application Ser. No. 15/443,732 filed on Feb. 27, 2017, which issued as U.S. Pat. No. 9,854,851 and is a continuation of application Ser. No. 14/943,560 filed on Nov. 17, 2015, which issued as U.S. Pat. No. 9,578,902 and is a continuation of application Ser. No. 14/308,215 filed on Jun. 18, 2014, which issued as U.S. Pat. No. 9,277,773 and is a continuation in part of application Ser. No. 13/289,016 filed on Nov. 4, 2011, which issued as U.S. Pat. No. 8,790,154. The patent applications identified above are incorporated herein by reference in their entirety to provide continuity of disclosure.

FIELD OF THE INVENTION

This invention relates to surgical drains and drain bulbs used for collecting fluids and more particularly a device worn around the abdomen of the patient used for supporting drain bulbs on the patient's body to prevent pulling on drain tubes inserted into the patient.

BACKGROUND OF THE INVENTION

Surgical drains are tubes used to remove lymphatic fluid, infected fluid, blood or other fluids in surgical wounds. Drains are used for a wide variety of surgical procedures including breast surgery, melanoma surgery, abdominoplasties, breast reductions and vascular surgery. Drains are commonly placed by surgeons to drain body fluid which accumulates in the space created by surgery, to remove infection, and/or to remove accumulated blood. Drain tubes are connected to reservoir bulbs used to collect fluids from a surgical site and incision. The drain bulbs are reservoirs connected to a flexible drainage tube sutured into place or affixed with adhesive at the site the drain exits the skin. Drain bulbs remove fluid from the surgical wound through negative pressure suction. Typically, drains are left in a surgical site for one or two weeks.

A problem commonly experienced by patient's and medical staff caring for the patients, is that the drain bulbs collecting the fluid can become heavy and pull on the site where the drain exits the skin. The length of the drainage tube causes the drains to be mobile and they can be pulled, thereby causing further injury and/or discomfort to the patient. The drain bulbs are difficult to manage in showers especially if there are multiple drains.

Therefore, a need exists for a drain support apron that holds drain bulbs securely to a patient's body to prevent the drain bulbs from falling or pulling unnecessarily on the patient's drain tubes.

SUMMARY OF THE INVENTION

The primary object of the present invention is to provide a drain support apron that fits comfortably around a patient's abdomen and provides secure storage for placement of one or more drain bulbs on the patient's body.

The present invention fulfills the above and other objects by providing a drain support apron having a main panel with a plurality of pockets located thereon that provide storage for one or more drain bulbs. The drain apron is preferably worn around a patient's midsection. Straps extend from side edges of the main panel of the drain support apron and are wrapped around the patient's midsection and back and secured on the patient's side, so the patient does not have to lay on the buckle or other attachment mechanism securing the two straps to each other. Elastic is located along an upper edge of each pocket to prevent the drain bulbs from falling out of the apron, which would cause unwanted pulling on the sutures holding the drain tubes in the surgical wound.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which:

FIG. 3 is a rear view of a drain support apron of the present invention being worn by a patient;

FIG. 4 is a side view of a drain support apron of the present invention being worn by a patient;

DESCRIPTION OF THE PREFERRED EMBODIMENTS

Figure 1:
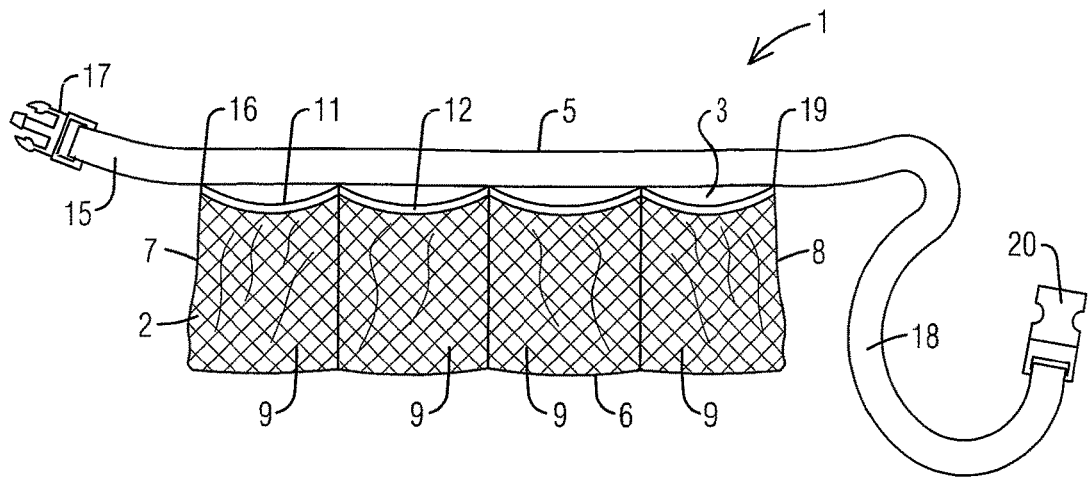
FIG. 1 is a front view of a drain support apron of the present invention.
Figure 2:
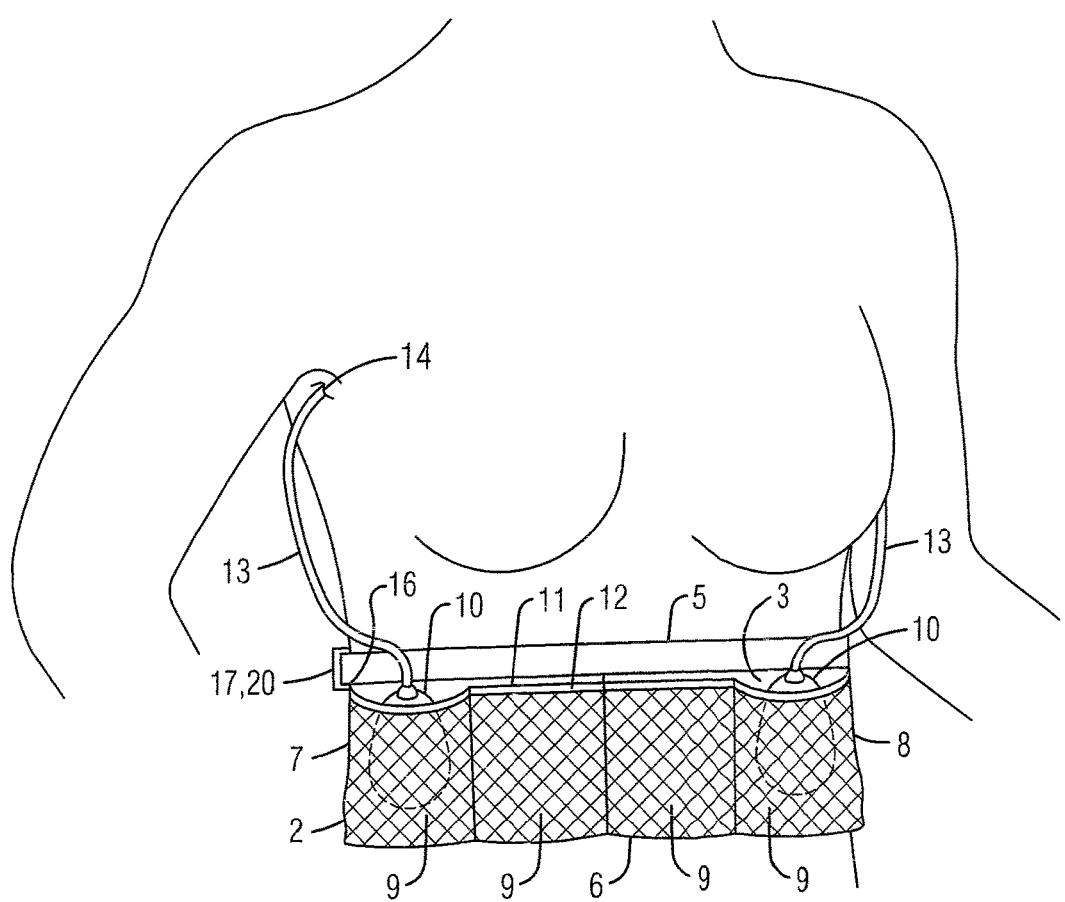
FIG. 2 is a front view of a drain support apron of the present invention being worn by a patient.

For purposes of describing the preferred embodiment, the terminology used in reference to the numbered accessories in the drawings is as follows:

1. drain support apron, generally
2. main panel
3. front surface of main panel
4. rear surface of main panel
5. top edge of main panel
6. bottom edge of main panel
7. first side edge of main panel
8. second side edge of main panel
9. pocket
10. drain bulb
11. top edge of pocket
12. elastomeric band
13. drain tube
14. surgical wound
15. shortened strap
16. first upper corner of main panel
17. first buckle
18. elongated strap
19. second upper corner of main panel
20. second buckle
21. extender strap
22. first extender strap buckle
23. second extender strap buckle With reference to FIGS. 1-5, the drain support apron 1 comprising a substantially rectangular-shaped main panel 2 having a front surface 3, rear surface 4, top edge 5, bottom edge 6, first side edge 7 and second side edge 8. A plurality of pockets 9 are located on the front surface 3 of the main panel 2 to provide storage for one or more drain bulbs 10. Said pockets 9 are preferably rectangular-shaped and located across the front surface 3 in a row extending upward from the bottom edge 6 of the main panel 2 a predetermined distance and terminating below the top edge 5 of the main panel 2, thereby leaving a portion of the front surface 3 of the main panel 2 located between the top edge 5 of the main panel 2 and a top edge 11 of the plurality of pockets 9 exposed. One or more elastomeric bands 12 are preferably located along the top edge 11 of each pocket 9 to prevent drain bulbs 10 from falling out of the drain support apron 1, which would cause unwanted pulling on any sutures holding drain tubes 13 in a surgical wound 14.

A shortened strap 15 extends from a first upper corner 16 of the first side edge 7 of the main panel 2 and has a first buckle 17 (such as a male or female end of a buckle) or equivalent attachment means located thereon. An elongated strap 18 extends from a second upper corner 19 of the second side edge 8 of the main panel 2 and has a second buckle 20 (such as a male or female end of a buckle) or equivalent attachment means located thereon. The first buckle 17 located on the shortened strap 15 and the second buckle 20 located on the elongated strap 18 are used to engage each other to secure the drain support apron 1 around a patient's midsection. The shortened strap 15 has a length that is shorter than the elongated strap 18. The shortened strap 15 in combination with the elongated strap 18 causes the first buckle 17 and second buckle 20 to be positioned on the patient's side so the patient does not have to lay on the first buckle 17 and second buckle 20 or equivalent attachment means securing the shortened strap 15 to the elongated strap 18. Alternatively, the first buckle 17 may be attached directly to the first side edge 7 of the main panel 2 or adjacent thereto via strapping or other attachment means necessary for attaching the first buckle 17 to the main panel 2. The shortened strap 15 having a length that is less than the elongated strap 18.

Figure 5:
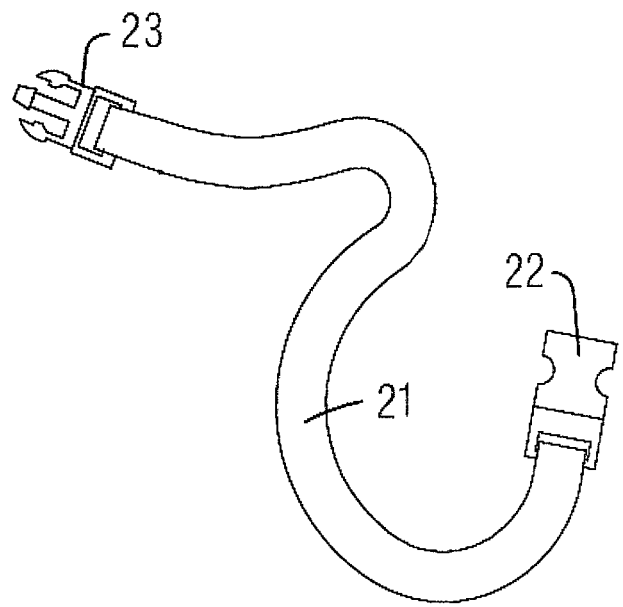
FIG. 5 is a front view of an extender strap of the present invention.
Figure 6:
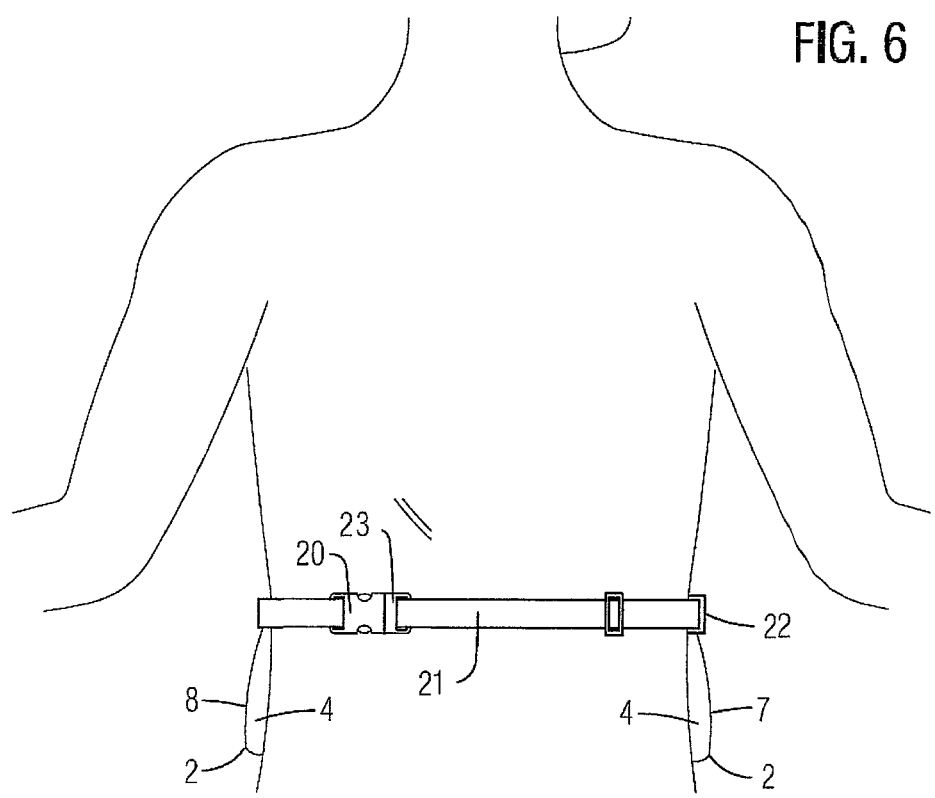
FIG. 6 is a rear view of a drain support apron and extender strap of the present invention being worn by a patient.

An extender strap 21, as illustrated in FIGS. 5 and 6, may be secured to the first buckle 17 and second buckle 20 of the shortened strap 15 and the elongated strap 18, respectively, via a first extender strap buckle 22' and a second extender strap buckle 23. The extender strap 21 may be used to accommodate larger patients wherein the drain support apron 1 would not fit around a patient's waste.

The main panel 2 is preferably constructed out of a non-stretchable water resistant material and/or quick drying material, such as nylon. The plurality of pockets 9, are preferably constructed out of a netting or mesh material having elastomeric qualities that allow the pockets 9 to stretch over any drain bulbs 10 inserted inside. The mesh material also allows the drain bulbs 10 and contents thereof to be visually inspected without having to remove the drain bulbs 10 from the pockets 9.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A drain support apron for surgical drain bulbs comprising:
    a substantially rectangular-shaped main panel having a front surface, a rear surface, top edge, bottom edge, first side edge and second side edge;
    a continuous row of rectangular-shaped pockets located across the front surface of the main panel and extending from the first side edge of the main panel to the second side edge of the main panel to provide storage for one or more surgical drain bulbs;
    a first strap extending from a first upper corner of the first side edge of the main panel;
    a first buckle located on the first strap;
    a second strap extending from a second upper corner of the second side edge of the main panel;
    a second buckle located on the first strap;
    said continuous row of rectangular-shaped pockets located across the front surface of the main panel extending upward from the bottom edge of the main panel a predetermined distance and terminating below the top edge of the main panel, thereby leaving a portion of the front surface of the main panel located between the top edge of the main panel and a top edge of the continuous row of rectangular-shaped pockets exposed;
    side edges of each rectangular-shaped pocket within said continuous row of rectangular-shaped pockets each abutting one another;
    an elastomeric band located along the top edge of said continuous row of rectangular-shaped pockets to prevent drain bulbs from falling out of the drain support apron;
    said main panel is constructed out of a non-stretchable material;
    said continuous row of rectangular-shaped pockets are all constructed out of a mesh material having elastomeric qualities; and
    said mesh material allowing drain bulbs placed within the continuous row of rectangular-shaped pockets to be visually inspected without having to remove the drain bulbs from the continuous row of rectangular-shaped pockets.

* * * * *